United States Patent
Pinchuk

(10) Patent No.: US 8,002,828 B2
(45) Date of Patent: Aug. 23, 2011

(54) METHOD OF IMPLANTATION USING POLYMER ADHESIVE FOR AN INTRAOCULAR LENS THAT MINIMIZES POSTERIOR CAPSULE OPACIFICATION

(76) Inventor: Leonard Pinchuk, Miami, FL (US)

( * ) Notice: Subject to any disclaimer, the term of this patent is extended or adjusted under 35 U.S.C. 154(b) by 1150 days.

(21) Appl. No.: 11/741,369

(22) Filed: Apr. 27, 2007

(65) Prior Publication Data

US 2007/0255403 A1    Nov. 1, 2007

Related U.S. Application Data

(60) Provisional application No. 60/745,944, filed on Apr. 28, 2006.

(51) Int. Cl.
  *A61F 2/16* (2006.01)
(52) U.S. Cl. ............... 623/6.12; 623/6.16; 623/6.62; 623/905
(58) Field of Classification Search .......... 623/6.12, 623/6.16, 6.34, 6.37, 6.62, 905
See application file for complete search history.

(56) References Cited

U.S. PATENT DOCUMENTS

| | | | | |
|---|---|---|---|---|
| 4,057,535 A | * | 11/1977 | Lipatova et al. | 528/68 |
| 4,740,534 A | * | 4/1988 | Matsuda et al. | 523/111 |
| 4,919,151 A | * | 4/1990 | Grubbs et al. | 128/898 |
| 5,002,571 A | * | 3/1991 | O'Donnell et al. | 623/6.11 |
| 5,098,444 A | * | 3/1992 | Feaster | 623/6.36 |
| 5,133,748 A | * | 7/1992 | Feaster | 623/6.12 |
| 5,278,258 A | | 1/1994 | Gerace et al. | |
| 5,391,590 A | | 2/1995 | Gerace et al. | |
| 6,231,603 B1 | * | 5/2001 | Lang et al. | 623/6.37 |
| 6,361,561 B1 | | 3/2002 | Huo et al. | |
| 6,613,343 B2 | | 9/2003 | Dillingham et al. | |
| 6,702,853 B1 | * | 3/2004 | Peyman | 623/6.39 |
| 6,713,583 B2 | | 3/2004 | Liao et al. | |
| 6,747,090 B2 | | 6/2004 | De Groot et al. | |
| 6,960,230 B2 | * | 11/2005 | Haefliger | 623/6.39 |
| 6,986,763 B2 | | 1/2006 | Holmen | |
| 7,156,101 B2 | | 1/2007 | Terwee et al. | |
| 7,559,949 B2 | * | 7/2009 | Pinchuk | 623/6.56 |
| 2002/0123793 A1 | * | 9/2002 | Schaldach et al. | 623/1.15 |
| 2005/0125059 A1 | | 6/2005 | Pinchuk et al. | |
| 2005/0228120 A1 | | 10/2005 | Hughes et al. | |
| 2006/0134177 A1 | * | 6/2006 | Liu et al. | 424/427 |
| 2007/0255403 A1 | * | 11/2007 | Pinchuk | 623/6.11 |

FOREIGN PATENT DOCUMENTS

| | | | |
|---|---|---|---|
| WO | WO/00/22459 | | 4/2000 |
| WO | WO/01/77197 | | 10/2001 |
| WO | WO 01/77197 A2 | * | 10/2001 |
| WO | WO 2004/011529 A1 | * | 2/2004 |
| WO | PCT/US2007/010292 | * | 11/2007 |
| WO | WO 2007/127400 A2 | * | 11/2007 |
| WO | WO 2007/127400 A3 | * | 11/2007 |

OTHER PUBLICATIONS

"Update on Accommodative IOLs", Howard Fine, MD, Michael Colvard, MD, H Burkhard Dick, MD, Cataract & Refractive Surgery Today, downloaded Apr. 4, 2006, www.crstodayarchive.com/03.

* cited by examiner

*Primary Examiner* — Paul Prebilic
(74) *Attorney, Agent, or Firm* — Gordon & Jacobson, PC

(57) ABSTRACT

Various polymers are provided that can be polymerized in the lens capsule with the ability to covalently bond an intraocular lens implant to the posterior capsule of the eye such that there is no space available between the intraocular lens implant and the lens capsule for lens epithelial cells to proliferate and thereby significantly reducing posterior capsule opacification.

15 Claims, No Drawings

METHOD OF IMPLANTATION USING POLYMER ADHESIVE FOR AN INTRAOCULAR LENS THAT MINIMIZES POSTERIOR CAPSULE OPACIFICATION

CROSS-REFERENCE TO RELATED APPLICATIONS

This application claims the benefit of provisional application Ser. No. 60/745,944 filed Apr. 28, 2006 which is herein incorporated by reference in its entirety.

BACKGROUND OF THE INVENTION

1. Field of the Invention

This invention relates to artificial lens implants for the eye.

2. State of the Art

An intraocular lens (IOL) is an artificial lens implanted into the lens capsule of the eye in place of the natural crystalline lens of the eye because it has been clouded over by a cataract or injured. When the natural lens is removed from the lens capsule of the eye, lens epithelial cells (LECs) begin to multiply and spread on the posterior capsule and effectively render the posterior capsule opaque. This opacification, commonly referred to as posterior capsule opacification (PCO), causes clouding of vision and can lead to blurring and possibly total vision loss. While the LECs can theoretically spread on the anterior wall as well, due to the large opening in the anterior capsule (the capsulorrhexus), there is no wall for them to spread onto.

The occurrence of PCO is relatively high in traditional IOL implantations where the LECs spread between the IOL and the lens capsule. There have been some IOL designs where the sharpness of the corners of the lens has prevented cellular migration under the lens; however, recent literature suggests that these geometrical features simply retard the progression of PCO. PCO occurs in approximately 40% of IOL recipients within two years of receiving a synthetic lens.

The usual treatment for PCO is laser ablation of the posterior capsule where a laser is used to vaporize the posterior capsule and the cells that adhere to it. However, in terms of health economics, PCO is very expensive to treat. Therefore, it is desirable to avoid PCO at the outset.

SUMMARY OF THE INVENTION

The present invention describes various polymers that can be polymerized in the lens capsule with the ability to covalently bond an IOL to the posterior capsule of the eye such that there is no space available between the IOL implant and the lens capsule for the LECs to proliferate and thereby significantly reducing PCO.

DETAILED DESCRIPTION OF THE PREFERRED EMBODIMENTS

U.S. application Ser. No. 11/741,239, now issued as U.S. Pat. No. 7,559,949, entitled "Injectable Intraocular Lens that Minimizes Posterior Capsule Opacification and Methods and Materials for Realizing Same," filed concurrently herewith is herein incorporated by reference in its entirety. The invention consists of a polymeric adhesive synthesized in the lens capsule that reacts with or otherwise adheres to an IOL implant and also reacts with the nucleophiles of the posterior capsule. The polymer adhesive bonds the IOL implant to the posterior capsule, thereby eliminating space between the IOL implant and the posterior capsule where cells can migrate and thus significantly reducing PCO.

In one embodiment, a thin layer of polymeric adhesive material is spread over the posterior capsule. The IOL implant is placed in contact with the thin layer of polymeric adhesive material. The thin polymeric adhesive material reacts with or otherwise adheres to the IOL implant and reacts with the nucleophiles of the posterior capsule to effectively bond the IOL implant to the posterior capsule, thereby eliminating space between the IOL implant and the posterior capsule where cells can migrate. PCO is thereby significantly reduced.

In another embodiment, the polymeric adhesive material is encapsulated in one or more breakable microcapsules and placed on the IOL implant. Subsequent breakage of the microcapsule(s) dispenses the polymeric adhesive material onto the posterior capsule. The polymeric adhesive material is synthesized in the lens capsule and reacts with the IOL implant and with the nucleophiles of the posterior capsule to effectively bond the IOL implant to the posterior capsule, thereby eliminating space between the IOL implant and the posterior capsule where cells can migrate. PCO is thereby significantly reduced.

Examples of the nucleophiles that exist on the posterior capsule include hydroxyl groups, amine groups, acid groups, sulfur groups and the like. Polymers that have the ability to react with the nucleophiles of the posterior capsule to thereby bind the IOL implant to the posterior capsule include i) a prepolymer of polyisobutylene with isocyanate end groups, ii) polyurethanes and polyurethaneureas, iii) epoxides, iv) cyanoacrylates, v) proteinacious polymers, vi) carbohydrates or polysaccharides, and v) silicon rubber with reactive end groups as described below in more detail.

Prepolymer of Polyisobutylene with Isocyanate End Groups

In accordance with the present invention, a prepolymer of polyisobutylene with isocyanate end groups is provided. The prepolymer can be bifunctional and linear or multifunctional and starred. The isocyanate-terminated prepolymer can be loaded into the first barrel of a two barrel syringe. A reactive co-polymer is loaded into the second barrel of the two barrel syringe. An exemplary reactive co-polymer is a prepolymer of polyisobutylene with hydroxyl or amine end groups. The syringe is preferably realized from polypropylene and is free of air, moisture and any other nucleophile. The isocyanate-terminated prepolymer and the reactive co-polymer are preferably clear with a refractive index between 1.40 and 1.53. The streams from the two barrels of the syringe are merged in a static mixer located on the exit of the syringe. The mixture produced at the exit of the syringe, which is typically a viscous fluid, is injected through the capsulorrhexus such that it covers the posterior capsule. The IOL implant is positioned in the lens capsule in contact with the mixture. Other mechanisms (e.g., breakable microcapsules) can be used to locate the mixture between the posterior capsule and the IOL implant. Within the lens capsule, the isocyanate-terminated prepolymer will react with the reactive co-polymer to form a gel-type adhesive film. Simultaneous to this polymerization reaction, the reactive isocyanates of the prepolymer component chemically react with the nucleophiles (amine groups) of the posterior capsule, thereby forming a chemical bond between the gel-type adhesive film and the posterior capsule by formation of urea linkage. Such chemical bonding permanently adheres the IOL implant to the posterior capsule and eliminates spaces where lens epithelial cells can migrate and cause PCO. The reaction between the isocyanates of the prepolymer component and the nucleophiles (amine groups) of the posterior capsule does not produce a byproduct that can otherwise be toxic to the eye. The resultant polymer of the gel-type adhesive film is preferably clear with a refractive index between 1.40 and 1.53.

Alternatively, the isocyanate-terminated prepolymer and the reactive co-polymer can be premixed prior to loading into a syringe and the contents injected through the capsulorrhexus such that it covers the posterior capsule. In this embodiment, slow reacting components must be used to enable flow through the syringe prior to polymerization.

Polyurethanes and Polyurethaneureas

Polyurethanes and polyurethaneureas are typically comprised of at least two components: an isocyanate-terminated prepolymer and a multinucleophilic co-polymer. An example of a polyurethane is the combination of a multiisocyanate such as the reaction product of a branched polytetramethylene macroglycol reacted with methylene bisphenyl diisocyanate (MDI) to provide a prepolymer that is isocyanate terminated. The multinucleophilic co-polymer can be the same macroglycol, such as polytetramethylene glycol that is terminated with hydroxyl groups. The hydroxyl groups of the multinucleophilic co-polymer react with the isocyanate groups of the multiisocyanate to produce a high molecular weight polyether urethane. This polyether urethane can be tailored to provide specific properties by adding chain extenders to the nucleophilic component of the polymer system, such as ethylene glycol and the like. Some polyurethanes are more stable than others in the body. U.S. Pat. No. 5,133,742, the details of which are herein incorporated by reference in its entirety, describes methods for increasing the biostability of these polymers.

In accordance with the present invention, a low molecular weight isocyanate-terminated prepolymer can be synthesized and loaded into the first barrel of a two barrel syringe. A hydroxyl-terminated co-polymer is loaded into the second barrel of the two barrel syringe. The streams from the two barrels of the syringe are merged in a static mixer (e.g., baffles) located on the exit of the syringe. The mixture produced at the exit of the syringe, which is typically a viscous fluid, is injected through the capsulorrhexus such that it covers the posterior capsule. The IOL implant is positioned in the lens capsule in contact with the mixture. Other mechanisms (e.g., breakable microcapsules) can be used to locate the mixture between the posterior capsule and the IOL implant. Within the lens capsule, the isocyanate-terminated prepolymer will react with the hydroxyl-terminated co-polymer to form a gel-type adhesive film. Simultaneous to this polymerization reaction, the reactive isocyanates of the prepolymer component chemically react with the nucleophiles of the posterior capsule, thereby forming a chemical bond between the gel-type adhesive film and the posterior capsule. Such chemical bonding permanently adheres the IOL implant to the posterior capsule and eliminates spaces where lens epithelial cells can migrate and cause PCO. The resulting gel-type adhesive film is preferably clear with a refractive index between 1.40 and 1.53.

Alternatively, the isocyanate-terminated prepolymer and the hydroxyl-terminated co-polymer can be premixed prior to loading into a syringe and the contents injected through the capsulorrhexus such that it covers the posterior capsule. In this embodiment, slow reacting components must be used to enable flow through the syringe prior to polymerization.

An exemplary hydroxyl-terminated co-polymer that can be used in this capacity is a polyisobutylene (PIB) diol as it will provide a rubbery polyurethane-based gel that is biostable. Other hydroxyl-terminated co-polymers are perfluropolyethyleneglycol polytetramethyleneglycol, poly(hexamethylene carbonate)diol, and the like. Preferably the macroglycol is biostable and has an index of refraction between 1.40 and 1.53.

Epoxies

Epoxies function in a manner similar to polyurethanes but include an epoxide-terminated prepolymer (rather than the isocyanate-terminate prepolymer) and a multinucleophilic co-polymer. The epoxide-terminated prepolymer and the multinucleophilic co-polymer are mixed and the resulting mixture is injected through the capsulorrhexus such that it covers the posterior capsule. The IOL implant is positioned in the lens capsule in contact with the mixture. Other mechanism can be used to locate the mixture between the posterior capsule and the IOL implant. Within the lens capsule, the epoxide-terminated prepolymer will react with the multinucleophilic co-polymer to form a gel-type adhesive film. Simultaneous to this polymerization reaction, the reactive epoxide groups of the prepolymer component chemically react with the nucleophiles of the posterior capsule, thereby forming a chemical bond between the gel-type adhesive film and the posterior capsule. Such chemical bonding permanently adheres the IOL implant to the posterior capsule and eliminates spaces where lens epithelial cells can migrate and cause PCO. The resulting gel-type adhesive film is preferably clear with a refractive index between 1.40 and 1.53.

Alternatively, the epoxide-terminated prepolymer and the multinucleophilic co-polymer epoxy can be premixed prior to loading into a syringe and the contents injected through the capsulorrhexus such that it covers the posterior capsule. In this embodiment, a slow reacting epoxy, such as the 5 minute epoxies, must be used to enable flow through the syringe prior to polymerization.

Suitable epoxies include glycidyl-terminated polytetramethylene glycol, glycidyl-terminated polyisobutylene, glycidyl terminated perfluroethyleneoxide, and the like.

Cyanoacrylates (CA)

In accordance with the invention, a polymeric material with cyanoacrylate end groups is provided that readily transforms to a soft rubbery gel (e.g., shore A=20) in the lens capsule upon contact with moisture and/or proteins within the lens capsule to form a gel-type adhesive film. Simultaneous to this polymerization reaction, the reactive cyanoacrylate groups chemically react with the nucleophiles of the posterior capsule, thereby forming a chemical bond between the gel-type adhesive film and the posterior capsule. Such chemical bonding permanently adheres an IOL implant to the posterior capsule and eliminates spaces where lens epithelial cells can migrate and cause PCO. The cyanoacrylate-terminated polymer as well as the resulting gel-type adhesive film are preferably clear with a refractive index between 1.40 and 1.53.

Suitable cyanoacrylate (CA) terminated materials that yield soft rubber-like gels upon contact with moisture and/or proteins within the lens capsule include:
  i) 3-arm star cyanoacrylate (CA)-telechelic PIB [Ø(PIB-CA)$_3$];
  ii) CA-PDMS-CA where PDMS is poly(dimethyl siloxane);
  iii) CA-PEG-CA where PEG is polyethylene glycol; and
  iv) CA-PEG-b-PDMS-b-PEG-CA.

A liquid form cyanoacrylate-based material (such as liquid CA-PDMS-CA) can be used as such (in bulk). Preferably, it is loaded into a syringe and injected into the lens capsule from the syringe. Alternatively, a non-fluid form cyanoacrylate-based material (such as crystalline PEG-based material) is preferably dissolved in a suitable solvent (such as DMSO, a non-protic, biocompatible FDA approved solvent) to render the prepolymer injectable. The cyanoacrylation method seems to be of general applicability and can be used for the cyanoacrylation of a great variety of hydroxide-containing molecules.

Aromatic silicone cyanoacrylates can also be used which have a higher refractive index. A PIB-based cyanoacrylate material can also be used. Such material has an even higher refractive index.

A table of other potential cyanoacrylate-based materials follows below. An initiator component (e.g., N,N-dimethyl-p-toluidine in n-$C_6H_{14}$) can also be mixed with a cyanoacrylate-based material to ensure completeness of the reaction that forms the gel-type intraocular lens. The Fn number in the chart below represents the functionality number of the polymer material and relates to the number of end groups per mole of the polymer material.

the lens capsule, the CA-terminated material undergoes a polymerization reaction that forms a gel-type adhesive film. Simultaneous to the polymerization reaction, the CA-terminated material reacts with the IOL implant and reacts with the nucleophiles of the posterior capsule to effectively bond the IOL implant to the posterior capsule, thereby eliminating space between the IOL implant and the posterior capsule where cells can migrate and thus significantly reducing PCO.

In another embodiment, the CA-based material is encapsulated in one or more breakable microcapsules and placed on the IOL implant and/or on the posterior capsule. The IOL implant is placed such that microcapsules are disposed between the IOL implant and the posterior capsule. Subsequent breakage of the microcapsule(s) dispenses the polymeric adhesive material onto the posterior capsule. The poly-

| Polymers | Visual appearance | MW (g/mol) | $F_n{}^a$ | Initiator | Remarks | Swelling test | Softness |
|---|---|---|---|---|---|---|---|
| CA—PIB—CA<br>\|<br>CA | light brown, highly viscous, not injectable by syringe | 4000 | 2.5 | N,N-dimethyl-p-toluidine in n-$C_6H_{14}$ | crosslinks upon contact with initiator sol fraction 15% in THF | 108% in hexanes | too soft to measure even by Shore A |
| | | | | egg yolk | crosslinks (hard to separate egg yolk and polymer) | | |
| CA—PIB—CA<br>\|<br>CA | light brown, low viscosity liquid, flows freely, injectable by syringe | 1330 | 2.9 | N,N-dimethyl-p-toluidine in n-$C_6H_{14}$ | crosslinks during storage within 2-3 days, sol fraction 5% in THF | 37% in hexanes | Shore A = 40 |
| | | | | glass surface (moisture) | crosslinks during storage within 2-3 days | | |
| CA-PDMS-CA | light brown, low viscosity liquid, flows freely, injectable by syringe | 5000 | 1.9 | N,N-dimethyl-p-toluidine in n-$C_6H_{14}$ | crosslinks during storage within 2-3 days, sol fraction 10% in THF | 360% in hexanes | too soft to measure even by Shore A |
| | | | | egg yolk | crosslinks (hard to separate egg yoLk and polymer) | | |
| | | | | glass surface (moisture) | crosslinks during storage within 2-3 days, sticks to glassware | | |
| CA-PEG-CA | brown solid | 2000 | 1.9 | glass surface (moisture) | soluble in DMSO, solution syringible, crosslinks upon contact with moisture, crosslinks during storage in less than 1 hr, becomes rubbery upon DMSO addition, solubility limit in DMSO: 50 wt % | 1010% (in water) 612% (in DMSO) | too soft to measure even by Shore A |
| CA-PEG-PDMS-PEG-CA | light brown, low viscosity liquid, flows freely, injectable by syringe | 4000 (PDMS = 40%) | 0.8 | N,N-dimethyl-p-toluidine in THF | crosslinks experiment to be repeated with $F_n$~2.0 triblock | | THF extracted product: too soft to measure even by Shore A |

In an exemplary embodiment, the CA-terminated material is applied as a thin layer to the posterior capsule. The IOL implant is placed in contact with the thin CA-terminated material. Upon contact with moisture and/or proteins within meric adhesive material is synthesized in the lens capsule. The polymeric adhesive material reacts with the IOL implant and reacts with the nucleophiles of the posterior capsule to effectively bond the IOL implant to the posterior capsule, thereby eliminating space between the IOL implant and the posterior capsule where cells can migrate and thus significantly reducing PCO.

Proteinacious Polymers and Carbohydrates or Polysaccharides

Proteinacious polymers can also be used in this invention. Here, slurries of collagen, elastin, and/or other peptides can be mixed with one or more cross-linking agents (such as formaldehyde, gluteraldehyde, carbodiimide and the like) and applied as a thin layer to the posterior capsule. The IOL implant is placed in contact with this thin layer. Other mechanisms (e.g., breakable microcapsules) can be used to locate the mixture between the posterior capsule and the IOL implant. Within the lens capsule, the cross-linking agent reacts with the proteinacious polymer to form a gel-type adhesive film. Simultaneous to this cross-linking reaction, the cross-linking agent chemically reacts with the nucleophiles of the posterior capsule, thereby forming a chemical bond between the gel-type adhesive film and the posterior capsule. Such chemical bonding effectively bonds the IOL implant to the posterior capsule and eliminates spaces where lens epithelial cells can migrate and cause PCO. The proteinacious polymer and the cross-linking agent(s) as well as the resulting gel-type adhesive film are preferably clear with a refractive index between 1.40 and 1.53.

Similarly, carbohydrate or polysaccharide gel-like materials can be used for this purpose. Such gel like materials can include alginate, pectin, carrageenan, gellan, starch and the like. The gel like materials are mixed with one or more cross-linking agents (such as multivalent cations including calcium chloride, barium chloride and the like; more permanent cross-linking agents can also be used including the epoxides and the multiisocyanates as described above). This mixture is applied as a thin layer to the posterior capsule. The IOL implant is placed in contact with this thin layer. Other mechanisms (e.g., breakable microcapsules) can be used to locate the mixture between the posterior capsule and the IOL implant. Within the lens capsule, the cross-linking agent reacts with the gel-like material to form a gel-type adhesive film. Simultaneous to this cross-linking reaction, the cross-linking agent chemically reacts with the nucleophiles of the posterior capsule, thereby forming a chemical bond between the gel-type adhesive film and the posterior capsule. Such chemical bonding effectively bonds the IOL implant to the posterior capsule and eliminates spaces where lens epithelial cells can migrate and cause PCO. The carbohydrate or polysaccharide gel-like materials and the cross-linking agent(s) as well as the resulting gel-type adhesive film are preferably clear with a refractive index between 1.40 and 1.53.

Silicone Rubber with Reactive End Groups

Prepolymers of silicone rubber can be made with reactive end groups (e.g., methoxy, ethoxy, acetoxy, hydrogen, chlorine and others) that can both initiate polymerization and react with tissue at the same time to effectively gel and bond the IOL implant to the posterior capsule. It is important that the reactive end group be non-toxic to the posterior capsule.

In an exemplary embodiment, the silicon-based material is applied as a thin layer to the posterior capsule. The IOL implant is placed in contact with the thin silcon-based adhesive layer. Simultaneous to the polymerization reaction, the adhesive layer reacts with the IOL implant and with the nucleophiles of the posterior capsule reactive to effectively bond the IOL implant to the posterior capsule, thereby eliminating space between the IOL implant and the posterior capsule where cells can migrate and thus significantly reducing PCO.

In another embodiment, the silicon-based material is encapsulated in one or more breakable microcapsules and placed on the IOL implant and/or on the posterior capsule. The IOL implant is placed such that microcapsules are disposed between the IOL implant and the posterior capsule. Subsequent breakage of the microcapsule(s) dispenses the polymeric adhesive material onto the posterior capsule. The polymeric adhesive material is synthesized in the lens capsule, and also reacts with the IOL implant and reacts with the nucleophiles of the posterior capsule to effectively bond the IOL implant to the posterior capsule, thereby eliminating spaces between the IOL implant and the posterior capsule where cells can migrate and thus significantly reducing PCO.

Although the polymeric adhesive material described herein employs a polymerization reaction to the nucleophiles (e.g., hydroxyl groups) of the posterior capsule to effectively bind thereto, this polymerization reaction can be initiated and continued with small amounts of water.

Use of a Tacky Polymer

In another embodiment, a tacky adhesive is placed on the IOL and the lens is pressed against the lens capsule. Here there is no physical bond between the lens and the IOL, rather they are coupled by hydrophobic interactions.

There are certain polymers that are both tacky and hydrophobic in nature and can be used to adhere an IOL to the lens capsule. Exemplary polymers include polybutadiene, polyisoprene or polyisobutylene polymers of molecular weight less than 100,000 Daltons; preferably between 500 and 30,000 Daltons. These polymers can be syringed onto the posterior or anterior walls of the lens capsule and an IOL pressed against it to effectively bond the IOL to the wall of the lens capsule. Although these bonds are non-reactive, the hydrophobic and tacky nature of the polymer will hold the IOL in place and provide a boundary which will prevent cells from migrating between the IOL and the lens capsule.

In another embodiment of the invention, an IOL can be bonded to the posterior wall of the lens capsule or the anterior wall of the lens capsule or alternatively, two IOLs can be used where one is attached to the posterior capsule and another to the anterior capsule. In this manner, the lenses are able to move closer or further apart from each other depending upon the pressure in the vitreous humour or upon the tension exerted on the lens capsule by the zonules. In this manner, the lenses behave like a telescope and will allow focusing of an image on the retina. In this manner, the eye is capable of accommodating. The adhesive provides both a means of supporting the IOLs as well as preventing epithelial cells from spreading between the lens capsule and the IOL.

There have been described and illustrated herein several embodiments of a polymeric adhesive material for bonding an intraocular lens implant to the posterior capsule of the eye in a manner that minimizes posterior or anterior capsule opacification. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed herein.

I claim:

1. A method of implantation comprising:
   inserting an intraocular lens implant into the lens capsule of the eye; and
   interposing a polymeric adhesive material between the intraocular lens implant and a capsulary wall, said polymeric adhesive material reacting with the intraocular lens and reacting with nucleophiles of the capsulary wall to bond the intraocular lens implant to the capsulary wall in a manner that reduces space between the intraocular lens implant and the capsulary wall;

wherein said polymeric adhesive material comprises polyisobutylene with isocyanate end groups.

2. A method according to claim 1, wherein:
said polymeric adhesive material reactively polymerizes within the lens capsule of the eye.

3. A method according to claim 1, wherein:
said polymeric adhesive material is applied as a thin layer to the capsulary wall.

4. A method according to claim 1, wherein:
said polymeric adhesive material is encapsulated in one or more breakable microcapsules that are interposed between the intraocular lens implant and the capsulary wall and then broken to dispense the polymeric adhesive material therebetween.

5. A method according to claim 1, wherein:
said capsulary wall comprises a posterior capsule wall.

6. A method according to claim 1, wherein:
said intraocular lens implant is an accommodating intraocular lens implant.

7. A method according to claim 6, wherein:
said intraocular lens implant includes first and second intraocular lens implant, wherein the first intraocular lens is bonded to an anterior capsule wall by the polymeric adhesive material in a manner that reduces space between the first intraocular lens implant and the anterior capsule wall, and wherein the second intraocular lens is bonded to a posterior capsule wall by the polymeric adhesive material in a manner that reduces space between the intraocular lens implant and the posterior capsule wall.

8. A method according to claim 1, wherein:
said polymer adhesive material includes a first polymer component and a second polymer component, the first polymer component including polyisobutylene with isocyanate end groups, and the second polymer component reacting with the first polymer component to form a gel-type film.

9. A method according to claim 8, wherein:
said second polymer component includes polyisobutylene with hydroxyl end groups.

10. A method according to claim 8, wherein:
said second polymer component includes polyisobutylene with amine end groups.

11. A method according to claim 8, further comprising:
mixing together the first and second polymer components before the interposing step.

12. A method according to claim 11, wherein:
the first and second polymer components are loaded into respective barrels of a syringe, the respective barrels merging to a static mixer located at the exit of the syringe such that a mixture of the first and second polymer components are produced at the exit of the syringe.

13. A method according to claim 8, wherein:
the first and second polymer components are encapsulated in one or more breakable microcapsules that are interposed between the intraocular lens implant and the capsulary wall and then broken to dispense the polymeric adhesive material therebetween.

14. A method according to claim 8, wherein:
the first and second polymer components react with one another within the lens capsule of the eye to form the gel-type film therein.

15. A method according to claim 8, wherein:
the first and second polymer components have a refractive index between 1.40 and 1.53.

* * * * *